(12) United States Patent
Kristiansson et al.

(10) Patent No.: US 7,520,108 B2
(45) Date of Patent: Apr. 21, 2009

(54) METHOD OF STERILIZING PACKAGES

(75) Inventors: Anders Kristiansson, Lund (SE); Lars Åke Näslund, Furulund (SE); Anders Hedse Olsson, Staffanstorp (SE)

(73) Assignee: Tetra Laval Holdings & Finance SA, Pully (CH)

( * ) Notice: Subject to any disclaimer, the term of this patent is extended or adjusted under 35 U.S.C. 154(b) by 0 days.

(21) Appl. No.: 11/808,875

(22) Filed: Jun. 13, 2007

(65) Prior Publication Data

US 2007/0283667 A1 Dec. 13, 2007

Related U.S. Application Data

(60) Provisional application No. 60/814,899, filed on Jun. 20, 2006.

(30) Foreign Application Priority Data

Jun. 13, 2006 (SE) .................................... 0601298

(51) Int. Cl.
  B65B 55/08 (2006.01)
  A61L 2/14 (2006.01)
(52) U.S. Cl. .............................. 53/426; 53/489; 53/267; 422/22
(58) Field of Classification Search .................. 53/425, 53/426, 489, 267, 284.5, 85, 86; 250/492, 250/492.3, 493; 422/22, 302
  See application file for complete search history.

(56) References Cited

U.S. PATENT DOCUMENTS

| 3,780,308 | A | * | 12/1973 | Nablo | 250/492.3 |
| 4,014,158 | A | * | 3/1977 | Rausing | 53/167 |
| 4,367,412 | A | * | 1/1983 | Cheever | 250/492.3 |
| 4,439,686 | A | | 3/1984 | Cheever | |
| 5,210,426 | A | * | 5/1993 | Itoh et al. | 250/492.3 |
| 5,489,783 | A | * | 2/1996 | Kristiansson | 250/492.3 |
| 5,983,604 | A | * | 11/1999 | Wilfong et al. | 53/449 |
| 6,039,922 | A | | 3/2000 | Swank et al. | |
| 6,085,492 | A | * | 7/2000 | Moller et al. | 53/426 |
| 6,139,796 | A | * | 10/2000 | Kristiansson et al. | 422/22 |
| 6,221,216 | B1 | | 4/2001 | Nablo et al. | |
| 6,464,937 | B2 | * | 10/2002 | Wicklund | 422/22 |

(Continued)

FOREIGN PATENT DOCUMENTS

CH 595 248 2/1978

(Continued)

OTHER PUBLICATIONS

Form PCT/ISA/210 (International Search Report) dated Jan. 10, 2007.

*Primary Examiner*—Paul R Durand
(74) *Attorney, Agent, or Firm*—Buchanan Ingersoll & Rooney PC

(57) ABSTRACT

A method for sterilizing at least partly formed packages with electron beam irradiation in a packaging machine involves sterilizing each of at least two at least partially separate areas of the package by way of a respective electron beam sterilizing device, with each of the sterilizing devices being adapted to characteristics of each respective one of the two areas, and also performing a respective relative movement between the package and each of the electron beam sterilizing devices, which movements are adapted for the sterilization of each respective one of the two areas with the sterilizing devices.

21 Claims, 6 Drawing Sheets

U.S. PATENT DOCUMENTS

Figure 1:
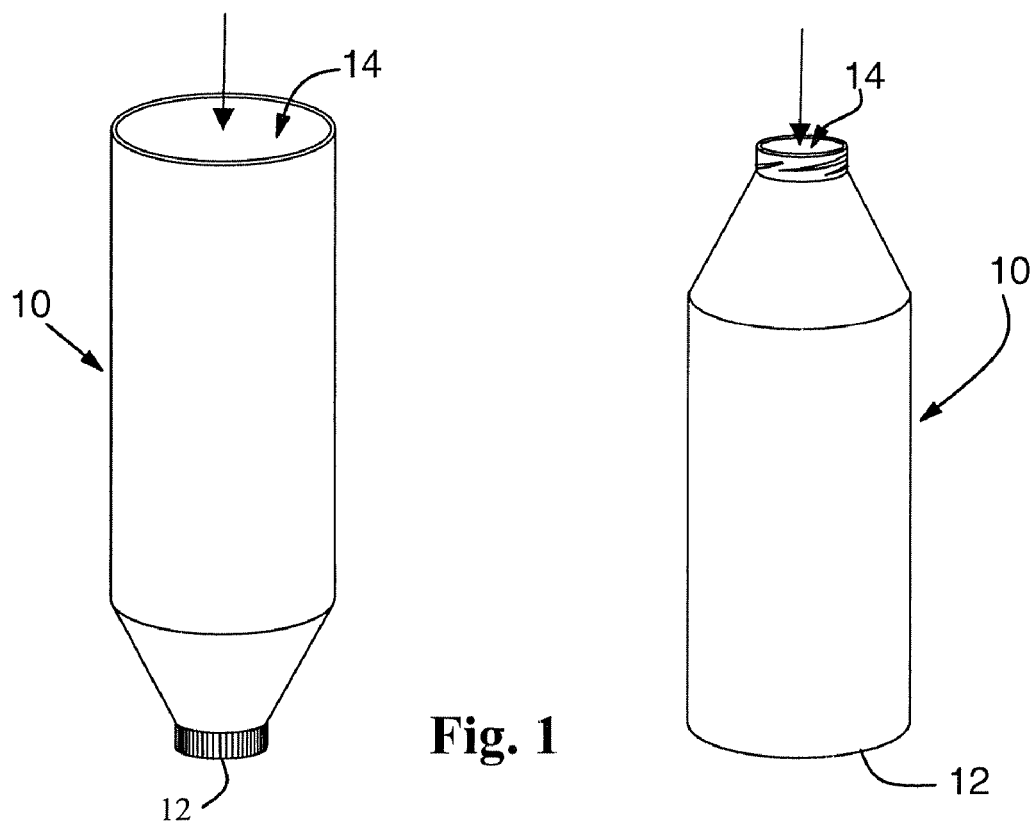

| | | | |
|---|---|---|---|
| 6,692,684 B1 * | 2/2004 | Nantin et al. | 264/521 |
| 6,698,162 B2 * | 3/2004 | Shudo et al. | 53/428 |
| 6,916,445 B2 * | 7/2005 | Centanni et al. | 422/22 |
| 6,929,040 B2 * | 8/2005 | Py | 141/329 |
| 6,949,222 B1 * | 9/2005 | Moller et al. | 422/62 |
| 7,051,906 B2 * | 5/2006 | Kis et al. | 222/568 |
| 7,078,716 B2 * | 7/2006 | Fink et al. | 250/492.3 |
| 2004/0060261 A1 * | 4/2004 | Py | 53/425 |
| 2005/0217211 A1 * | 10/2005 | Py | 53/426 |
| 2006/0159583 A1 | 7/2006 | Naslund et al. | |
| 2008/0138243 A1 | 6/2008 | Kristiansson et al. | |

FOREIGN PATENT DOCUMENTS

| | | |
|---|---|---|
| EP | 1 232 760 A1 | 8/2002 |
| EP | 1 356 828 A1 | 10/2003 |
| EP | 1 481 693 A2 | 12/2004 |
| EP | 1 481 693 A3 | 12/2004 |
| EP | 1 518 563 A1 | 3/2005 |
| FR | 2.140.393 | 1/1973 |
| GB | 1 470 990 | 4/1977 |
| GB | 1 525 484 | 9/1978 |
| JP | 2002-171949 | 6/2002 |
| JP | 2002-308229 A | 10/2002 |
| WO | WO 96/40297 A1 | 12/1996 |
| WO | WO 98/42385 A1 | 10/1998 |
| WO | WO 00/55884 A1 | 9/2000 |
| WO | WO 02/075771 A1 | 9/2002 |
| WO | 2005/002973 A1 | 1/2005 |

* cited by examiner

METHOD OF STERILIZING PACKAGES

This application is based on and claims priority under 35 U.S.C. § 119(e) with respect to U.S. provisional application No. 60/814,899 filed on Jun. 20, 2006, the entire content of which is incorporated herein by reference.

TECHNICAL FIELD

The disclosed subject matter generally pertains to sterilization of packaging material. More particularly, the subject matter relates to a method for sterilizing at least partly formed packages in a packaging machine.

TECHNICAL BACKGROUND

Within the food packaging industry, packages formed from blanks of packaging material have been used for quite a long time. The packaging material typically comprises different layers of paper or board, liquid barriers of, for example, polymers and gas barriers of, for example, thin films of aluminium. The blanks are preformed from a material web, which sometimes is provided with a pattern of crease lines facilitating forming and folding of packages. The web is cut into pieces, with each piece having a size and shape for making one package. After cutting, each piece is folded into a flat tube-formed blank having its longitudinal edges overlapping each other. Next, the longitudinal edges are sealed by any appropriate, conventional sealing technology such as for example heat sealing. The result is a flat tube-formed blank. Forming a blank from a web is well known per se and will not be described in further detail.

In the packaging machine, the blank is raised to form a tube usually having a square or rectangular cross section depending on the type of package. Thereafter, one end of the tube can be transversally sealed forming a bottom (or top) of the package and the package is ready to be filled with a product, for example food products like, for instance, beverages. These kinds of packages are marketed by the applicant under the trade name Tetra Rex®.

There are also carton bottle packages made from a tube-formed sleeve of a packaging material, as described above, and a plastic top sealed to the sleeve. The tops are either pre-made outside the packaging machine or injection-moulded directly on the sleeve in the packaging machine. The tops are provided with closures. These types of packages can be filled before the bottom end of the sleeve is transversally sealed and final folded to a bottom. They can also be filled through the pour opening of the closure. Packages like this are marketed by the applicant under the trade names Tetra Aptiva® and Tetra Top®.

Partly formed packages that are open in one end for filling but sealed to form a bottom or top at the other end, are commonly denoted Ready-To-Fill packages (RTF packages). Hereinafter, ready-to-fill packages will be denoted with the wording "packages".

To extend the shelf-life of the products being packed, it has been known to sterilize packages before the filling operation. Depending on the length of shelf-life desired and whether the distribution and storage is made at chilled or ambient temperature, different levels of sterilization can be chosen. However, the term sterilize as used herein comprises any level of cleaning and microbiological killing.

One way of sterilizing is to irradiate the inside of the package by electrons emitted from an electron beam unit. Such a method, and a device for realizing the method, is disclosed in International Application Publication No. WO 2005/002973, the disclosure of which is incorporated herein by reference.

An example of a system for sterilizing packages by electron beam technology includes an electron beam sterilizing device for emitting an electron beam along a path. The device is connected to an electron beam generator that is connected to a high voltage power supply and a filament power supply. The latter transforms power from the high voltage power supply to a suitable input voltage for a filament of the generator. The filament can be housed in a vacuum chamber. In operation, electrons $e^-$ from the filament are emitted along an electron beam path in a direction towards a target. A grid around the filament is used for diffusing the electron beam into a more uniform beam, and for focusing the electron beam towards the target. Beam absorbers and magnetic fields can also be used to shape the electron beam. The electrons exit the sterilizing device through an electron exit window.

However, when sterilizing packages, it has been found that it is difficult to achieve a uniform electron beam dose throughout the entire package with one electron beam sterilizing device. This is because of the different shapes of the physical portions of the package. Corners, openings, closures, bottle-like top portions, bottoms, flat walls and the like need to be sufficiently sterilized, but preferably without being over-exposed to irradiation. There is also a cost consideration involved in that it is preferable to not be forced to use more energy than necessary.

SUMMARY

The method disclosed here permits sterilization of at least partly formed packages with electron beam irradiation in a packaging machine in a manner which achieves a substantially uniform dose on the desired portions of the package (e.g., all portions of the package). To achieve a predetermined sterilisation level of all desired portions of the package, such portions should be exposed to a predetermined electron beam dose. The method disclosed here makes this possible.

A method for sterilizing at least partly formed packages with electron beam irradiation in a packaging machine, and for subsequently filling and sealing the package, comprises sterilizing at least two areas of an inside surface of the package by way of a respective electron beam sterilizing device for each of the two areas, with the sterilizing devices being adapted to characteristics of each respective one of the two areas, and providing a respective relative movement between the package and each of the two electron beam sterilizing devices, which movement is adapted for the sterilization of each respective one of the two areas with the sterilizing devices. Thereafter, the package is transported to a filling station where the package is filled with a product through an opening in the package, and the opening in the package is then sealed.

In this way one suitable sterilizing device can be chosen for each area to be sterilized. In other words, the sterilization can be optimized in that the configuration of each sterilizing device can be adapted to the characteristics, such as shape, size etc., of the corresponding area. In addition to adapting the configuration of the sterilizing device, the relative movement between the package and the sterilizing device is also adapted. Even if a sterilizing device is adapted for a certain area, some areas may need a longer exposure time or a slower movement of the electron beam than others to be sufficiently sterilised. By combining an adapted sterilizing device with an adapted relative movement, the sterilization of the package can be made very effective in terms of energy and time consumption. The combination also makes it possible to achieve a cost effective sterilizing system.

The method can also involve sterilizing additional areas by providing an electron beam sterilizing device for each of the areas, with the sterilizing devices being adapted to the characteristics of each respective one of the areas, or purposes of sterilization, the package can be thought of as being divided into any number of areas, and the packaging machine may be provided with a corresponding number of sterilizing devices. In this way a very careful irradiation of the package can be performed.

The method can also include dividing at least the inside surface of the package in such a way that the formed areas are at least slightly overlapping each other. By doing this, it can be assured that at least no portion of the inside of the package is left un-sterilized. In some cases an area may be more or less completely overlapping another.

For sterilizing an area, the sterilizing device is preferably connected to an electron beam generator. The electron beam generator can be housed in the sterilizing device to form a compact unit which is easy to move and handle.

For sterilization of several areas, at least some of the sterilizing devices can be connected to the same or a common electron beam generator. If suitable, a number of sterilizing devices can be connected to the same electron beam generator. This saves space and may be more cost-effective than having one electron beam generator per sterilizing device.

In a further aspect, for sterilization of multiple areas, all of the sterilizing devices can be connected to the same or a common electron beam generator.

The sterilizing of the areas can be carried out by sterilizing devices each provided with at least one electron exit window for exiting at least a portion of an electron beam generated by the at least one electron beam generator. The electron beam exit window is used for exiting the electrons and is an important parameter for adapting a sterilizing device to an area. Different window configurations give different characteristics of the irradiation.

At least first and second treatment stations can be provided in a sterilizing chamber, each arranged with at least one electron beam sterilizing device. The method can involve arranging the package in the first station and sterilizing at least a first area of the inside of the package with the electron beam sterilizing device in the first treatment station, and arranging the package in the second treatment station and sterilizing at least a second area of the inside of the package with the electron beam sterilizing device in the second treatment station.

The method can further involve arranging the package in at least one additional treatment station, with the additional treatment station being arranged in the sterilizing chamber and provided with at least one electron beam sterilizing device, and sterilizing at least an area comprising a portion of the outside of the package near the opening thereof. In this way recontamination from the outside of the package and into the package can be avoided or prevented.

More than one package can be sterilized in each treatment station. In this way the capacity of the packaging machine can be increased.

According to another aspect, a method for sterilizing at least partly formed packages with electron beam irradiation in a packaging machine and for subsequently filling and sealing the package comprises relatively moving the package and a first electron beam sterilizing device to locate the first electron beam sterilizing device relative to the package at a position permitting irradiation of a first area of the package, sterilizing the first area of the package by irradiating the first area with an electron beam through operation of the first electron beam sterilizing device, relatively moving the package and a second electron beam sterilizing device to locate the second electron beam sterilizing device relative to the package at a position permitting irradiation of a second area of the package at least partially different from the first area of the package, sterilizing the second area of the package by irradiating the second area with an electron beam through operation of the second electron beam sterilizing device, moving the package to a filling station, filling the package with a product through an opening in the package, and sealing the opening in the package after the filling.

BRIEF DESCRIPTION OF THE DRAWING FIGURES

In the following, a presently preferred embodiment will be described in greater detail with reference to the enclosed drawing figures, wherein like reference numerals are used to designate like elements, in which:

FIG. 1 schematically shows two partly formed packages to be sterilized by the method disclosed herein.

Figure 2:
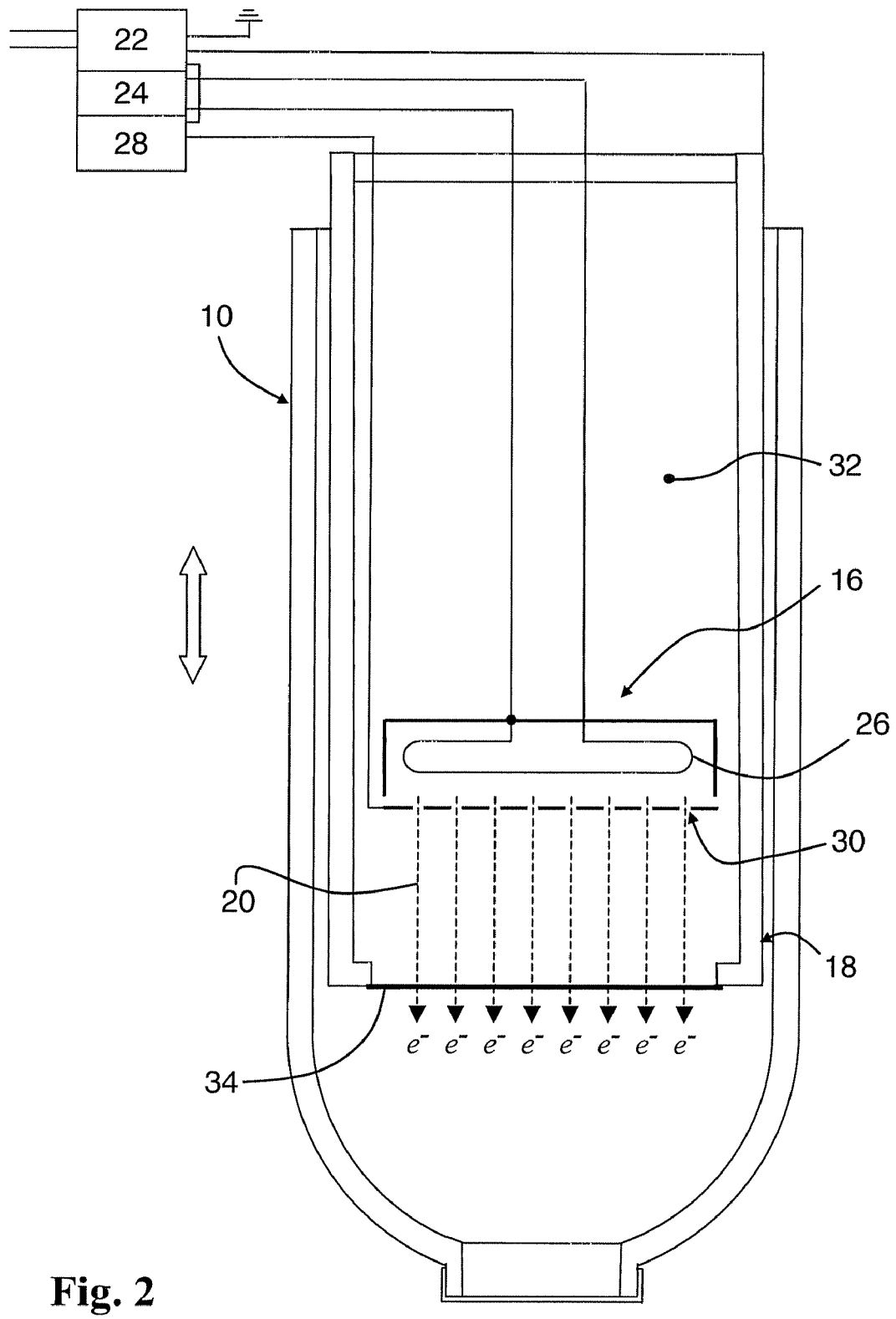

FIG. 2 schematically shows an example of a system for carrying out the method.

Figure 3:
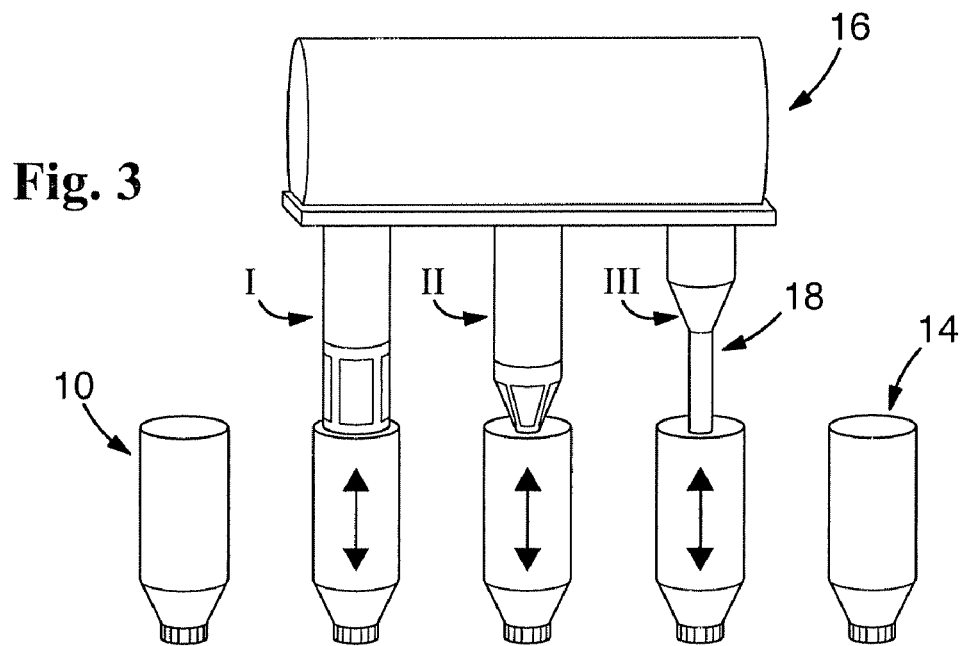

FIG. 3 schematically shows a view of a number of sterilizing devices connected to a common electron beam generator.

Figure 4:
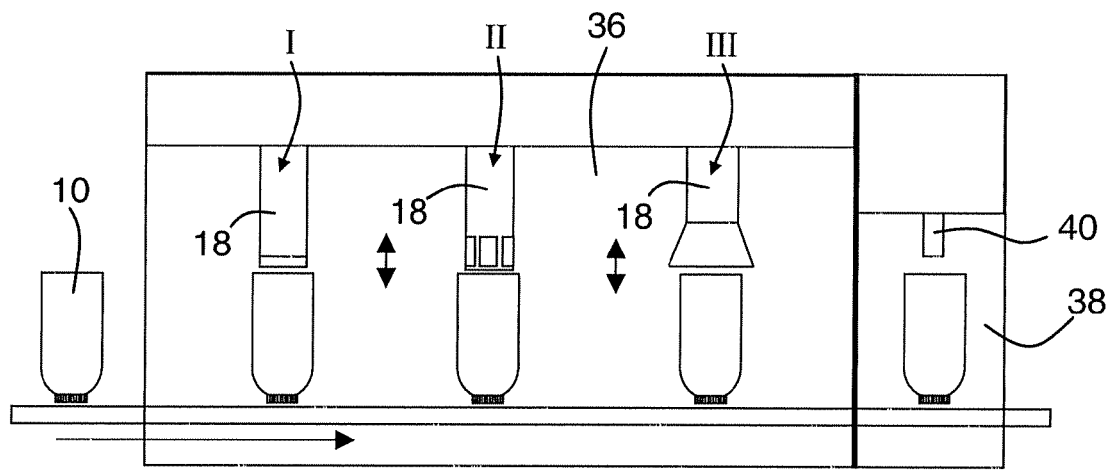

FIG. 4 schematically shows a view, partly in cross section, of a sterilizing chamber comprising three treatment stations, each provided with one sterilizing device, and a filling chamber.

Figure 5:
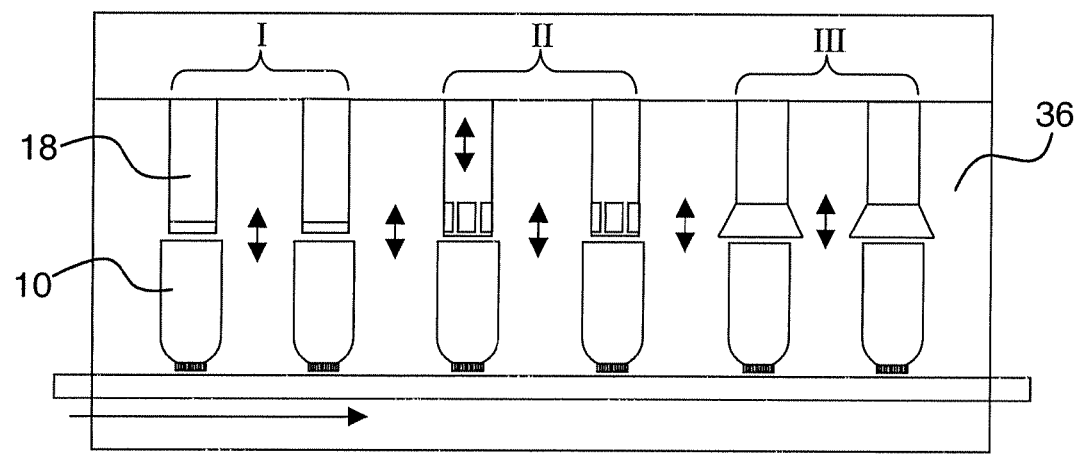

FIG. 5 schematically shows a view similar to that of FIG. 4, but with two sterilizing devices in each treatment station.

FIGS. 6a-f schematically show different embodiments of sterilizing devices, with each sterilizing device being shown in a view from outside, a view partly in cross section and a view from the axial end provided with the exit window configuration.

For simplicity, similar features in the different embodiments will be denoted with the same reference numerals.

DETAILED DESCRIPTION

FIG. 1 shows two embodiments of partly formed packages 10 to be sterilized by the method disclosed herein. As mentioned in the introduction, partly formed packages are normally closed at one end 12 and have an opening 14 at the other end. The closed end 12 can be formed as a bottom or top and the opening 14 can be an open end of a package sleeve, which later will be sealed, or for example a pour opening surrounded by a neck of a closure, which later will be provided with a cap or the like. The package embodiment to the right in the figure has a sealed bottom end and an opening in the top in the form of a pour opening surrounded by the threaded neck of a closure. The package embodiment to the left has an open (bottom) end and is provided at the other end with a top and a sealed closure.

In the following, and with reference to FIG. 2 illustrating an electron beam generator 16 and an electron beam sterilizing device 18, a description of electron beam sterilization will be briefly described. The electron beam generator 16 comprises means for emitting an electron beam 20 along a path and is connected to the sterilizing device 18 which distributes the beam 20 to the package 10.

Normally, an electron beam generator 16 is connected to a high voltage power supply 22, suitable for providing sufficient voltage to drive the electron beam generator 16 for the desired application. The electron beam generator 16 is also connected to a filament power supply 24, which transforms power from the high voltage power supply 22 to a suitable input voltage for a filament 26 of the generator 16. In addition, the high voltage power supply 22 includes a grid control 28 for controlling a grid 30 of the electron beam generator 16.

Electron beam generators used in the sterilization of packages are generally denoted low voltage electron beam units, which units normally have a voltage below 300 kV. In the disclosed design the accelerating voltage is in the order of 70-90 kV. This voltage results in kinetic (motive) energy of 70-90 keV in respect of each electron.

The filament 26 can be made of tungsten and can be housed in a vacuum chamber 32. In an exemplary embodiment, the vacuum chamber can be hermetically sealed. In operation, an electrical current is fed through the filament 26 and the electrical resistance of the filament causes the filament to be heated to a temperature in the order of 2000° C. This heating causes the filament 26 to emit a cloud of electrons e$^-$. The electrons are emitted along an electron beam path in a direction towards the target area, in this case an area in the package 10. The grid 30, placed between the filament and the electron beam exit window, is provided with a number of openings and is used for diffusing the electron beam 20 into a more uniform beam, and for focusing the electron beam 20 towards the target area.

In the embodiment shown, the electron beam generator means is housed in the electron beam sterilizing device 18. The sterilizing device 18 comprises a vacuum chamber, which in this case is the same vacuum chamber as the vacuum chamber 32 of the electron beam generator 16. The sterilizing device 18 is further provided with an electron exit window 34. The window 34 can be made of a metallic foil, such as for example titanium, and can have a thickness in the order of 4-12 μm. A supporting net formed of aluminium or copper supports the foil from inside of the electron beam generator 16. The electrons exit the vacuum chamber 32 through the exit window 34.

In this embodiment, the sterilizing device 18 with the electron beam generator 16 inside has the form of a cylinder with a substantially circular cross section and the exit window 34 is located at a first end of the cylinder.

In another embodiment, shown in FIG. 3, the electron beam generator 16 and the sterilizing device 18 are of course connected, but only the sterilizing device 18 is cooperating with the package 10, i.e., the sterilizing device 18 is, at least to a portion, positioned or moved either inside or around the package 10 during irradiation. The vacuum chambers are then in communication with each other, and the sterilizing device 18 functions as an extension, or nozzle, of the electron beam generator 16, i.e., it is used to reach the package portions to be sterilized.

A support is provided for supporting the target, i.e., the package 10, within the target area. The support can for example be a conventional carrier of a conveyor which transports the package 10 through a sterilization chamber. During sterilization of a package 10 like the one to the left of FIG. 1, the package 10 may be placed upside down (i.e., the top is located downwards) in the support.

Further, during sterilization a relative movement is performed between the package 10 and the sterilizing device 18. Either the sterilizing device 18 is lowered into or around the package 10, or the package 10 is raised to surround the device 18, or both are moved towards one another. To accomplish this, the support may be either stationary or adapted to perform a motion towards and away from the sterilizing device 18.

In the second end of the sterilizing device 18 incorporating the electron beam generator 16, there are means provided for fastening it to a preferred element in the surroundings. For example, such means can be means for suspending the sterilizing device or the electron beam generator from the inner top wall of a sterilization chamber with the electron beam exit window 34 facing downwards in a direction towards the package 10. Alternatively, the second end is provided with means for providing a relative motion (see arrow) between the package 10 and the sterilizing device 18 for bringing them to a position or in a motion in which the device 18 is located at least partly in or around the package 10 for treating it.

The relative movement can be made in many different ways. For example, it can comprise a slow lowering of the sterilizing device into the package followed by a short stop and a quick raise out of the package. Alternatively, the relative movement may comprise a lowering and a raising without any stop. In a further alternative, the lowering and the raising is made very quick, but with a number of short stops along the way.

FIG. 4 shows a sterilization chamber 36 through which packages 10 are transported, in the direction of the horizontal arrow, to be sterilized. To extend the shelf-life of the products being packed, it has been known to sterilize packages before the filling operation. Depending on how long of a shelf-life is desired and whether the distribution and storage is made in chilled or ambient temperature, different levels of sterilization can be chosen. For ambient temperature, sterilization to a level which is denoted as commercially sterile is preferred. However, the term sterilize is here used to comprise any level of cleaning and microbiological killing.

FIG. 4 also shows a filling chamber 38. The packages 10 are transported to the filling chamber 38 after they have been sterilized in the sterilization chamber 36. The filling chamber 38 is provided with at least one filling station 40 for filling the packages 10 with a product through an opening thereof. As previously mentioned, the opening can either be a still open end of the package or a portion of a still not sealed closure, such as for example a pour opening surrounded by a neck.

The filling station 40 can be part of any suitable type of package filling system. For example a linear filling system or a rotary filling system can be used. The filling system will not be described in more detail.

The sterilization method disclosed here can involve theoretically dividing at least the inside surface of the package 10 in at least two areas to be sterilized. Each of the areas is sterilized by a respective electron beam sterilizing device 18. By using a number of sterilizing devices 18 and treating an area of a package 10 at a time, each sterilizing device 18 may be adapted to the characteristics, such as shape and size, of the area which it will sterilize. This means that each sterilizing device 18 can be substantially optimised for the area it will irradiate, i.e., it will be adapted to provide an electron beam 20, or a portion thereof, in a path suitable for the particular area to be sterilized. For this purpose, the sterilization chamber 36 is provided with at least two electron beam sterilizing devices 18 for the at least two areas.

An area is here defined as the surface or the surfaces of a package for which a sterilizing device is adapted. The division into areas can be made in any suitable way. For example, an area can have the form of a package bottom portion. Another area can have the form of a package inside envelope surface portion. Yet another area can have the form of a closure or a package top portion. However, the division is not necessarily bound by the physical portions of a package. An area can, for example, be made up of a portion of the bottom and a portion of the lower end of the inside envelope surface.

Another area can, for example, be made up of a closure and a top portion of the package. Yet another area can, for example, be made up of an envelope surface and a bottom portion of a package. The package portions and surfaces included in one area do not need to be continuous or connected, they may be entirely separated from each other. The number of different sterilizing devices needed is dependent on the number of different areas present in the package.

The areas may at least slightly overlap each other to help ensure that no portion of the package is given too low an electron beam dose. In some cases, an area may be more or less completely overlapping another. It will later be described a sterilizing device adapted for sterilizing a top portion area of a package. However, the dose over a closure area at the top portion may need to be boosted by another sterilizing device to be sufficiently sterilized. The second area will then be completely overlapping the first one.

Each sterilizing device 18 is configured for optimal irradiation of the assigned area which it will irradiate. The features of the sterilizing device 18 that can be modified to achieve the different irradiation characteristics needed for the different areas are for example the shape and size of the sterilizing device 18 and the number of electron beam exit windows 34 and their placement and shape. To further change the characteristics of the electron beam 20, the filament 26 and the control grid 30 can be modified.

Further, the relative movement between the package 10 and the sterilizing device 18, which is schematically shown by vertically arranged arrows in FIG. 4, is configured for optimal irradiation together with the sterilizing device 18.

In the embodiment shown in FIG. 4, the sterilizing chamber 36 is provided with a first and a second treatment station I, II. The description below will also point out that an additional station, in this case a third station III, can also be provided in the sterilizing chamber 36.

The first station I is a station in which a first area of the package 10 is to be sterilized and the second station II is a station in which a second area of the package 10 is to be sterilized. Each of the stations I, II comprises one electron beam sterilizing device 18 for sterilizing the respective area (s).

The sterilizing devices 18 in the stations of FIG. 4 can be separate sterilizing devices each connected to their own electron beam generator. The electron beam generator 16 may then be housed in the vacuum chamber 32 of the respective sterilizing device 18. Alternatively, the sterilizing devices 18 can be connected to a common electron beam generator 16 as shown in FIG. 3. However, for the sake of clarity, it should be noted that the stations in FIG. 3 are shown as to be provided with other sterilizing devices than the ones shown in FIG. 4.

In the embodiment of FIG. 4, the first station I is used for sterilizing an area comprising the inside of a top portion and the inside of a closed closure. The second station II is used for sterilizing an area in the form of the package inside envelope (peripheral) surface.

The sterilizing device 18 in the first station I will be described in more detail later with reference to FIG. 6a. It comprises a flat exit window for creating a wide circular beam suitably used for irradiating an area in the form of, for example, a dome-like package top portion. The sterilizing device 18 in the second station II, which will later be described with reference to FIG. 6d, is provided with multiple electron beam exit windows arranged for creating an electron beam suitably used for irradiation of, for example, a circular envelope surface of a package 10.

As mentioned earlier, the sterilizing chamber 36 can also comprise an additional or third station III for sterilizing at least a portion of the outside of the package 10 near an opening thereof before filling of the package 10. Such a sterilizing device 18 will later be described in more detail with reference to FIG. 6f.

A package 10, arranged with its top directed downwards, is entering the sterilizing chamber 36 to the left in FIG. 4 and is transported to the first treatment station I. In the first treatment station 1, the first sterilizing device 18 is lowered a suitable distance into the package 10, from the shown raised position, and irradiates the first area of the package 10. The area is exposed to the irradiation for a predetermined time, which time is dependent on the relative movement between the package 10 and the sterilizing device 18. After the pre-determined time, the sterilizing device 18 is raised again, and the package 10 is transported to the second treatment station II where the second area is irradiated by the sterilizing device 18 in said station II. The sterilizing device 18 is lowered and raised in a similar way. The relative movement, and thereby the irradiation exposure time, can be similar to or other than in the first station.

After the second treatment station II, the package is transported to the third station III in which an area in the form of at least a portion of the outside of the package 10, near the open end thereof, is sterilized to prevent recontamination of the inside of the package. Similarly, the sterilizing device 18 is lowered around the open end 12 of the package 10 and is sterilized during a predetermined time. The sterilizing device 18 is then raised and the sterilization of the package 10 is finalized. The package 10 is then ready to proceed to the next chamber, the filling chamber 38, to be filled. After filling, the package 10 is sealed. In this case the package 10 is sealed in that the open end 12 of the package sleeve is squeezed and transversally sealed by heat in a conventional way.

In an alternative embodiment, where the package is sterilized and filled through a pour opening at the top of the package (see the package to the right in FIG. 1), the sealing procedure comprises providing the neck, and surrounding or closing the pour opening with a membrane and/or a cap, such as for example a screw cap.

FIG. 5 shows a second embodiment of the sterilization chamber 36 in FIG. 4. In this second embodiment there is provided treatment stations each comprising more than one electron beam sterilizing device 18 of the same kind. In this way it is possible to sterilize more than one package at a time in each station. Preferably, the sterilizing devices 18 can be connected to a common electron generator like the one shown in FIG. 3. The packaging machine needs to provide double-indexing of the packages, i.e., a package 10 being at the first sterilizing device 18 in the first station I is transported directly to the first sterilizing device 18 in the second station II.

In the following a number of sterilizing devices 18 will be described having different electron beam characteristics due to, for example, different shapes and window configurations.

Figure 6A:
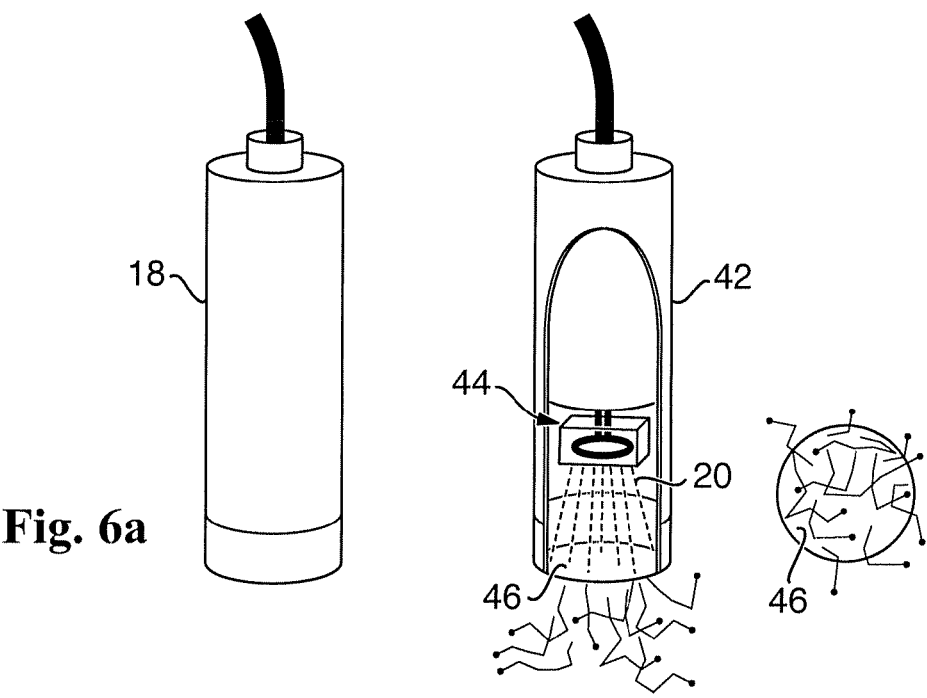

A first sterilizing device 18, shown in FIG. 6a, has a cylindrical, circular body 42 of a size corresponding to the size of a package having a circular cross section. The cylindrical body 42 surrounds an electron beam generator 44, and the filament and the grid of the generator is schematically shown in the drawing figure. In one axial end of the cylindrical body an electron beam exit window 46 is provided. In this embodiment the window 46 is flat, circular and of a size substantially corresponding to the circular end of the body 42. The filament can either be ring-shaped or in the form of a straight line. The grid is adapted to diffuse the electron beam 20 into a more uniform beam, and to focus the electron beam 20 towards the exit window 46 in a manner making the electron beam exit the window substantially through its entire surface or through selected portions of it. This configuration is suitably used for irradiating, for example, an area in the form of a flat bottom portion of a package. The sterilizing device 18 is then lowered into the package from an open top end of the package, or the package is raised to surround the sterilizing device. Alternatively, this sterilizing device 18 can be used for irradiating an area in the form of a circular symmetric or dome-like package top portion. The sterilizing device 18 is then lowered into the package from an open bottom end of the package, or the package is raised to surround the sterilizing device 18. Alternatively, the area is formed both by a bottom and an inside envelope surface of a package. The relative movement may then comprise a slow lowering of the sterilizing device and a short stop near the bottom of the package.

Figure 6B:
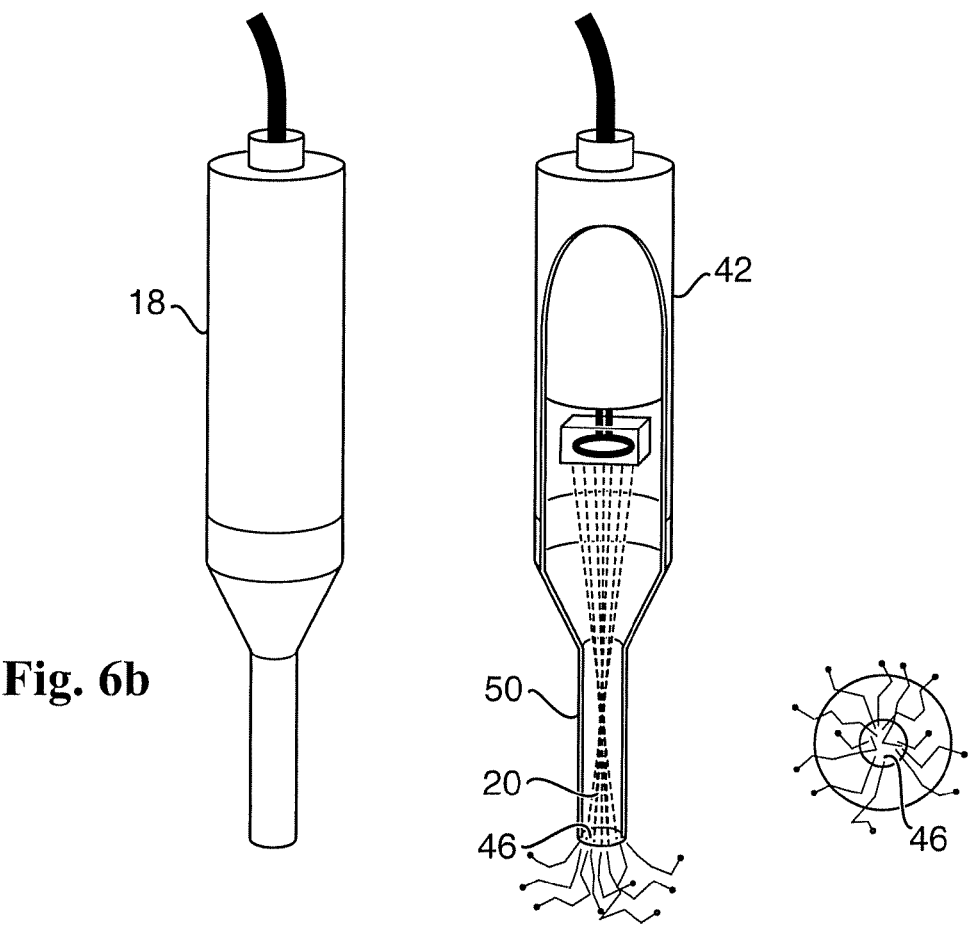

A second sterilizing device 18, shown in FIG. 6b, is substantially similar to the first one, but the body 42 is provided with a narrow, circular nozzle 50. The electron beam exit window 46 is placed in one of the axial ends and is flat and circular. The sterilizing device 18 can be used for irradiating packages such as bottles with a narrow open end through which the sterilizing device needs to be lowered and raised. A configuration like this can also be used for boosting the electron beam 20 in a particular area such as over a small area in the form of for example openings or closures and other irregularities. It should be understood that the shape of the nozzle may be other than circular, for example it can be square-formed, rectangular, triangular, oval or have any other shape.

Figure 6C:
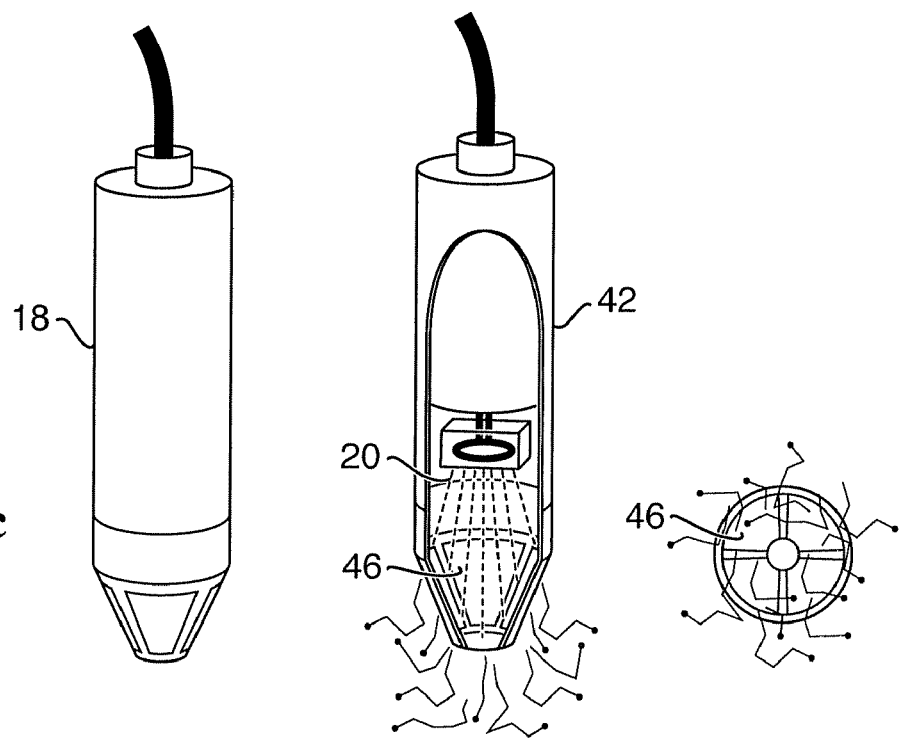
Figure 6D:
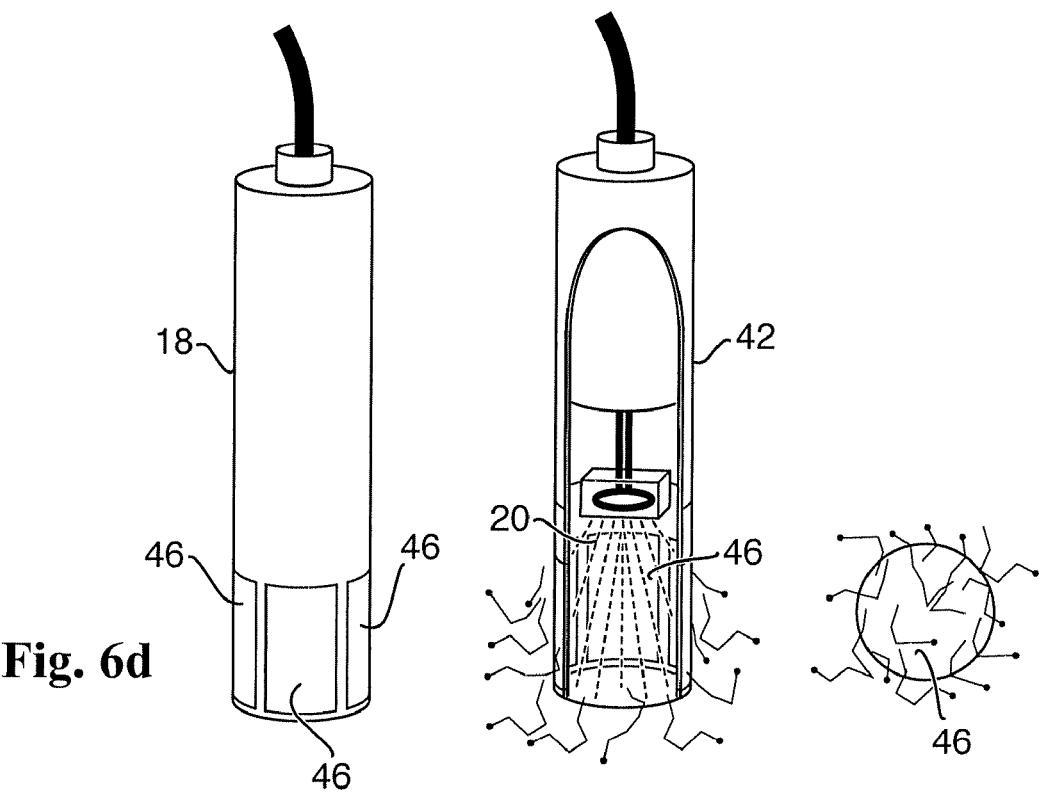

A third sterilizing device 18, shown in FIG. 6c, is also substantially similar to the first sterilizing device in its basic design, but is provided with multiple exit windows 46 arranged in a cone-shaped configuration for creating a wide circular beam 20 with boosted dose in the direction of each window 46. If four windows 46 are arranged, like shown, the sterilizing device 18 is suitably used for irradiating a symmetric, square package with corners. To provide a uniform dose on the inside of the package, the windows are preferably arranged to face the corners. This configuration is also suitable for irradiation of a circular inside envelope surface. Compared to the configuration in the first sterilizing device, this configuration will be faster when sterilizing the envelope surface of cylindrical packages since the average electron path length is shorter.

A fourth sterilizing device 18, shown in FIG. 6d, is substantially similar to the previous one and is also provided with multiple windows 46. The windows 46 are arranged in the envelope surface of the cylindrical, circular body 42. A window 46 may also be provided in the end of the body. The electron beam 20 created is spread both downwards and sidewards, and the sterilizing device 18 is suitably used for irradiation of an area comprising both a substantially flat package bottom and an inside envelope surface of the package.

Figure 6E:
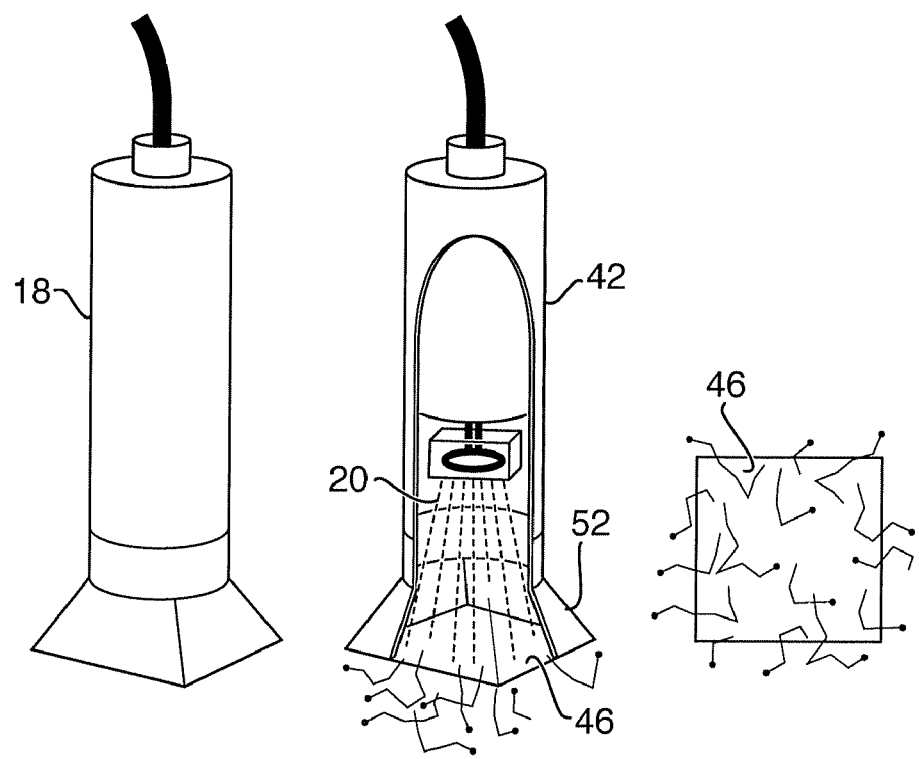

A fifth sterilizing device 18, shown in FIG. 6e, is substantially similar to the first one, but is provided with an axial square-shaped flat electron beam exit window 46. The size of the window 46 is larger than the cross section of the circular body 42. Therefore, the end arranged with the window 46 is provided with a flange 52. The end of the flange 52 connected to the circular body 42 is circular and the end provided with the window 46 is square-shaped. The grid is adapted to focus the electron beam 20 towards the exit window 46 to make the electron beam 20 exit the window 46 substantially through its entire surface or selected portions thereof. This configuration is suitably used for irradiating an area in the form of a square-shaped bottom portion of a package or a square-shaped inside surface of a package. Alternatively, the window 46 has another shape, such as elliptic or cross-shaped, for irradiation of correspondingly shaped packages.

Figure 6F:
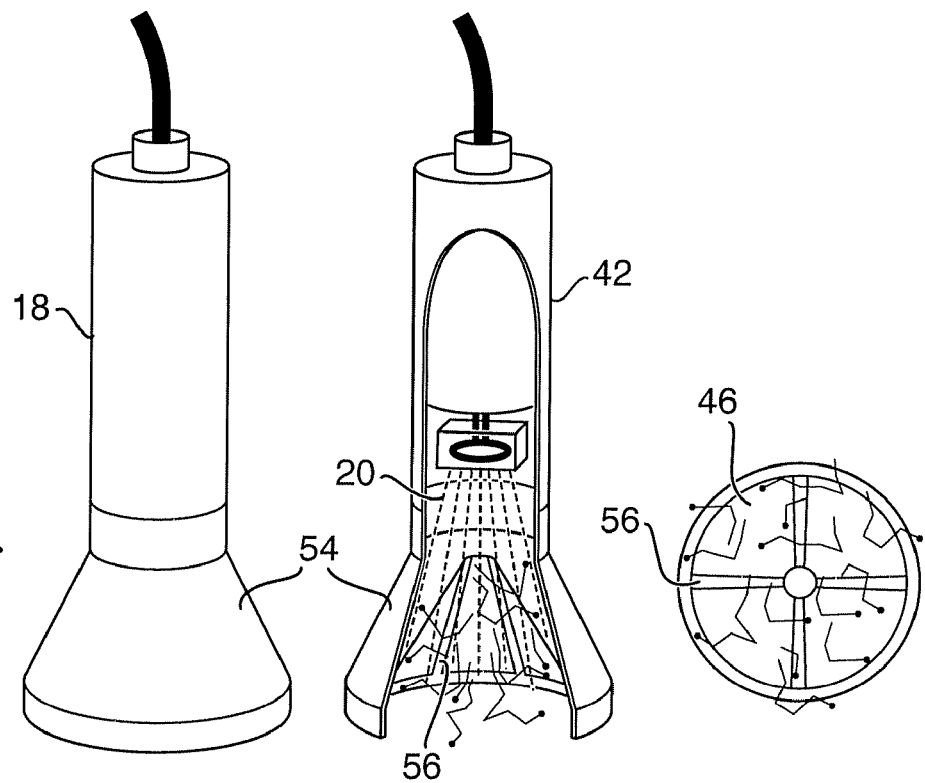

A sixth sterilizing device 18, shown in FIG. 6f, is substantially similar to the previous devices, but has a difference in that it can be suitably used for irradiation of non-flat shapes. At an end of the circular body 42 a funnel-shaped portion 54 is provided. The width of the funnel-shaped portion 54 is increasing in a direction away from the body 42. On the inside of the funnel-shaped portion 54, multiple electron exit windows 46 are arranged in a cone-shape 56. The cone-shape 56 tapers in a direction towards the body 42. In this way the exit windows 46 can be moved close to a package surface, even if the surface has a bulging form or if it is provided with a protruding closure. Preferably, an area in the form of the outside of a bottle-like top portion of a package can be irradiated by this device. Further, cups can also be irradiated.

In the method disclosed here, for example, at least the first and second sterilizing devices can be used for sterilizing a package like the one to the left in FIG. 1. The first sterilizing device sterilizes an area comprising the envelope surface and the top portion surface, whereas the second sterilizing device gives an extra boost to an area in the form of the inside of the closure. The sixth sterilizing device can be added for sterilizing an area comprising a portion of the outside surface of the package near the opening 14. The relative movement is adapted to each area.

Although the present invention has been described with respect to presently preferred embodiments, it is to be understood that various modifications and changes may be made without departing from the object and scope of the invention as defined in the appended claims.

In an additional embodiment two treatment stations are combined. For example, the first and second stations are provided at the same position for sterilizing the package first with an electron beam sterilizing device of the first station and then sterilizing the package with an electron beam sterilizing device of the second station. The package is not transported anywhere between the irradiation doses, but the sterilizing devices are instead either shifted once during a package stop or provided together. In the example of FIG. 4, it can for example instead be provided with two sterilizing devices in the first station, in reality making it two stations. A first sterilizing device may be adapted to sterilize an area in the form of the inside of the closure and a second sterilizing device may be adapted to sterilize an area in the form of the top portion, i.e., the area around the closure. Likewise, for example, the second station and the additional, third station can be combined. The sterilizing devices may then be arranged for example one around the other.

Further, packages have been described as having an inside envelope surface, and it is shown in the figures that the packages has a circular cross section. However, it should be understood that the wording package inside envelope surface should be interpreted as the inside wall or walls of the package, irrespective of the package cross section. The package cross section can have almost any shape such as round, square, rectangular, oval, triangular, orthogonal or other shape.

The invention claimed is:

1. Method for sterilizing at least partly formed packages with electron beam irradiation in a packaging machine and for subsequently filling and sealing the package, comprising:

sterilizing at least two areas of an inside surface of the package by way of at least two electron beam sterilizing devices, each said electron beam sterilizing device sterilizing a respective one of the at least two areas, the sterilizing devices being adapted to characteristics of each respective one of the two areas;

providing a respective relative movement between the package and each of the two electron beam sterilizing devices, which movement is adapted for the sterilization of each respective one of the two areas with the sterilizing devices;

transporting the package to a filling station;

filling the package with a product through an opening in the package; and sealing the opening in the package after the filling.

2. Method according to claim 1, further comprising sterilizing at least one additional area of the package by way of a further electron beam sterilizing device that is adapted to characteristics of the additional one area of the package.

3. Method according to claim 2, wherein at least some of the two electron beam sterilizing devices and the further electron beam sterilizing device are connected to a common electron beam generator.

4. Method according to claim 1, wherein the at least two areas partially overlap one another.

5. Method according to claim 1, wherein the sterilization of the at least two areas by way of the two electron beam sterilizing devices comprises sterilizing the at least two areas with the two electron beam sterilizing devices that are each connected to an electron beam generator.

6. Method according to claim 1, wherein the sterilization of the at least two areas by way of the two electron beam sterilizing devices comprises sterilizing the at least two areas with the two electron beam sterilizing devices that are connected to a common electron beam generator.

7. Method according to claim 1, wherein the sterilizing devices that sterilize the at least two areas each comprise at least one electron exit window through which exits at least a portion of an electron beam generated by at least one electron beam generator.

8. Method according to claim 1, further comprising sterilizing one of the at least two areas with a first one of the electron beam sterilizing devices at a first treatment station in a sterilizing chamber and sterilizing the other one of the at least two areas with a second one of the electron beam sterilizing devices in the sterilizing chamber.

9. Method according to claim 8, further comprising sterilizing more than one package simultaneously at each of the first and second treatment stations.

10. Method according to claim 1, further comprising:

positioning the package at a first treatment station and sterilizing one of the at least two areas of the package with one of the electron beam sterilizing devices;

moving the package to a second treatment station and sterilizing the other one of the at least two areas with a second one of the electron beam sterilizing devices.

11. Method according to claim 10, further comprising moving the package from the second treatment station to a third treatment station and sterilizing an additional area of the package at the third treatment station by way of a further electron beam sterilizing device.

12. Method according to claim 11, wherein the additional area of the package comprises at least a portion of an outside of the package adjacent the opening in the package.

13. Method according to claim 1, wherein the package comprises a closed end positioned opposite the open end, and wherein the respective relative movement between the package and each of the two electron beam sterilizing devices comprises providing relative movement in a direction from one of the closed end and the open end to the other of the closed end and the open end.

14. Method for sterilizing at least partly formed packages with electron beam irradiation in a packaging machine and for subsequently filling and sealing the package comprising:

relatively moving the package and a first electron beam sterilizing device to locate the first electron beam sterilizing device relative to the package at a position permitting irradiation of a first area of the package;

sterilizing the first area of the package by irradiating the first area with an electron beam through operation of the first electron beam sterilizing device;

relatively moving the package and a second electron beam sterilizing device to locate the second electron beam sterilizing device relative to the package at a position permitting irradiation of a second area of the package at least partially different from the first area of the package;

sterilizing the second area of the package by irradiating the second area with an electron beam through operation of the second electron beam sterilizing device;

moving the package to a filling station after the sterilizing of the first area of the package and after the sterilizing of the second area of the package;

filling the package with a product through an opening in the package; and sealing the opening in the package after the filling.

15. Method according to claim 14, further comprising, before filling the package, relatively moving the package and a third electron beam sterilizing device to locate the third electron beam sterilizing device relative to the package at a position permitting irradiation of a third area of the package at least partially different from the first and second areas of the package, and sterilizing the third area of the package by irradiating the third area with an electron beam through operation of the third electron beam sterilizing device.

16. Method according to claim 14, wherein the first and second areas of the package partially overlap one another.

17. Method according to claim 14, wherein the first and second electron beam sterilizing devices are connected to a common electron beam generator.

18. Method according to claim 14, wherein the first and second sterilizing devices each comprise at least one electron exit window through which exits at least a portion of an electron beam generated by at least one electron beam generator.

19. Method according to claim 14, further comprising sterilizing the first and second areas of the package in a common sterilizing chamber.

20. Method according to claim 14, further comprising:

positioning the package at a first treatment station and sterilizing the first area with the first electron beam sterilizing device;

moving the package to a second treatment station spaced from the first treatment station and sterilizing the second area of the package with the second electron beam sterilizing device.

21. Method according to claim 20, further comprising moving the package from the second treatment station to a third treatment station and sterilizing a third area of the package at the third treatment station through operation of a third electron beam sterilizing device.

* * * * *